United States Patent [19]

Strycker

[11] 4,057,645

[45] Nov. 8, 1977

[54] SUBSTITUTED PHENOXYALKYL QUATERNARY AMMONIUM COMPOUNDS AS ANTIARRHYTHMIC AGENTS

[75] Inventor: Stanley J. Strycker, Midland, Mich.

[73] Assignee: The Dow Chemical Company, Midland, Mich.

[21] Appl. No.: 648,554

[22] Filed: Jan. 12, 1976

Related U.S. Application Data

[62] Division of Ser. No. 484,525, Juy 1, 1974, Pat. No. 3,932,664, which is a division of Ser. No. 164,086, July 19, 1971, Pat. No. 3,875,215.

[51] Int. Cl.$^2$ ..................... A61K 31/14; A61K 31/24
[52] U.S. Cl. .................................. 424/329; 424/309
[58] Field of Search ............................. 424/309, 329; 260/567.6 M

[56] References Cited

U.S. PATENT DOCUMENTS 2,895,995  7/1959  Willey et al. ..................... 260/567.6
3,453,313  7/1969  Margot et al. ...................... 260/459

FOREIGN PATENT DOCUMENTS 2,017,497  11/1970  Germany.

OTHER PUBLICATIONS

Hey; Brit. J. Pharmacol. 7, (1952), pp. 117–129.
Hey; et al; Brit. J. Pharmacol. 9, (1954), pp. 471–475.
Jones et al; Biochem. J. 45 (1949), pp. 143–149.

*Primary Examiner*—Allen J. Robinson
*Attorney, Agent, or Firm*—James William Ambrosius

[57] ABSTRACT

Quaternary ammonium compounds such as [2-(4-amino-2,6-dibromophenoxy)ethyl]dimethyl (allyl) ammonium bromide are prepared by the reaction of a tertiary amine such as 3,5-dibromo-$\beta$-dimethylamino-p-phenetidine with a substituted organic compound such as allyl bromide. The quaternary ammonium compounds are useful in alleviating or inhibiting cardiac arrhythmias when the quaternary ammonium compounds, or compositions comprising the same are administered to animals.

6 Claims, No Drawings

SUBSTITUTED PHENOXYALKYL QUATERNARY AMMONIUM COMPOUNDS AS ANTIARRHYTHMIC AGENTS

CROSS-REFERENCE TO RELATED APPLICATION

This is a division, of application Ser. No. 484,525, filed July 1, 1974, now U.S. Pat. No. 3,932,664, which is a division of application Ser. No. 164,086, filed July 19, 1971, U.S. Pat. No. 3,875,215.

BACKGROUND OF THE INVENTION

The compounds of the present invention are substituted phenoxyalkyl quaternary ammonium compounds. Various other phenoxyalkyl quaternary ammonium compounds have been described by Hey, Brit. J. Pharmacol. 7, 117 (1952); Hey and Willey, Brit. J. Pharmacol. 9, 471 (1954) and U.S. Pat. No. 2,895,995; and by Jones et al., Biochem. J. 45, 143, (1949).

SUMMARY OF THE INVENTION

This invention is directed to quaternary ammonium salt compounds, and to a method and composition utilizing such compounds. More particularly, the invention is concerned with quaternary ammonium salt compounds corresponding to the formula:

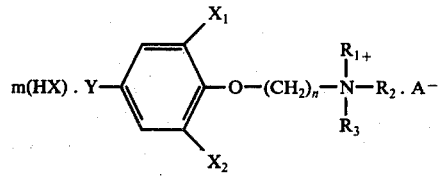

wherein Y represents amino, loweralkylamino or diloweralkylamino; $R_1$ and $R_2$ represent lower alkyl; $R_1$ and $R_2$ independently taken together represent an aliphatic hydrocarbon moiety of from 4, to 5, to 6 carbon atoms, which can be substituted with zero, one, or two lower alkyl substituents, $R_1$, $R_2$ and the quaternary nitrogen forming a 5, 6 or 7-membered ring; $R_3$ represents lower alkenyl, phenacyl, mono-, di or trihalophenacyl, lower alkynyl, substituted lower alkyl, substituted lower alkenyl or substituted lower alkynyl in which such moieties are substituted with one substituent selected from halogen, phenyl, halophenyl, dihalophenyl, trihalophenyl, nitrilo, hydroxy, carboxyalkyl and keto; or $R_1$, $R_2$ and $R_3$ taken together represent a quinuclidine residue; $X_1$ and $X_2$ both represent halogen; $A^-$ represents a stoichiometric equivalent quantity of a pharmaceutically-acceptable anion; $n$ represents one of the integers 2, 3 or 4; HX represents a stoichiometric equivalent quantity of a pharmaceutically-acceptable acid; and $m$ represents one of the intergers zero and one. The quaternary ammonium salt compounds are crystalline solids which are soluble in water, and of varying degrees of solubility in organic liquids such as dimethyl formamide, esters, halohydrocarbons, alcohols and the like.

In the present specification and claims, the term "halogen" is employed with respect to the moieties $X_1$, $X_2$ and $R_3$ of the above formula to designate one of the halogens chlorine, bromine and iodine, and the term "lower alkyl" is employed to designate lower alkyl of from 1, to 2, to 3, to 4, to 5, to 6 carbon atoms, the term "carboxyalkyl" is employed to designate such moieties containing from 2, to 3, to 4, to 5 carbon atoms. The terms "lower alkenyl" and "lower alkynyl" are employed to designate such moieties containing from 2, to 3, to 4, to 5, to 6 carbon atoms. The terms "pharmaceutically-acceptable anion" and "pharmaceutically-acceptable acid" as herein employed, refer to non-toxic anions or acids employed in quaternary ammonium salt compounds or acid-addition salts thereof. The terms include the acidic or anionic moieties which have no substantial toxicity or detrimental pharmacological effect when a quaternary ammonium salt compound including such an anion is administered to animals at dosages consistent with good pharmacological activity and acids of such moieties. Such pharmaceutically-acceptable anions include non-toxic inorganic anions such as the chloride, bromide, iodide, sulfate, nitrate, bisulfate or phosphate, or organic anions such aa the acetate, propionate, succinate, malate, fumarate, glutamate, salicylate, maleate, tartrate or citrate anions, organic sulfonate anions such as the camphorsulfonate, methanesulfonate, benzenesulfonate or toluenesulfonate anions. The methanesulfonate, benzenesulfonate, chloride and bromide anions are particularly useful in the preparation, purification and use of the quaternary ammonium salts of the invention and are preferred pharmaceutically-acceptable anions.

The compounds of the invention are useful in the study of drug effects upon cardiac activity in animals, and have been found to be particularly useful as antiarrhythmic agents. The compounds can be employed in combatting cardiac arrhythmias in animals by administering an antiarrhythmic amount of one or more of the quaternary ammonium salt compounds to an animal. In such use, the compounds are administered internally to the animal to introduce the compound into the animal's cardiovascular system. The compounds can be administered parenterally by intraperitoneal, subcutaneous or intravenous injection, for example, and typically by intravenous injection. In contrast to many known quaternary ammonium compounds, the quaternary ammonium salt compounds of the invention can also be administered to animals via the gastrointestinal tract, typically by oral administration. The compounds have excellent antiarrhythmic activity both therapeutically, in administration to an animal suffering from a cardiac arrhythmia, and prophylactically to protect an animal against the occurrence or recurrence of arrhythmias, typically in an animal subject to arrhythmias.

The terms "arrhythmic", cardiac arrhythmia" and "arrhythmia" as employed herein refer to irregular cardiac activity characterized by irregular beating of the heart, that is, non-rhythmic heart beat. Such arrhythmias involve substantial departures from the regular, substantially sinus (sinusoidal) normal heart beat. Arrhythmias are generally beyond the normal increased, but still substantially regular, heart beat rate resulting from physical activity. The term is inclusive of the conditions described by terms such as ventricular fibrillation, ventricular tachycardia, atrioventricular nodal beats, auricular flutter, auricular fibrillation or premature ventricular contractions. The terms "arrhythmic animal" and "arrhythmic mammal", as employed in the present specification and claims, mean and refer to animals suffering cardiac arrhythmias. Such arrhythmias can be the result of physiological or pathological conditions. They can also be brought about by physical conditions such as electrical stimulation or physical injury or they can result from pharmacological effects such as the administration of compounds such as digitalis or similar compounds such as ouabain, acetyl strohanthidin, deslanoside C or digitoxin; epinephrine; ergot; chloroform; cyclopropane and the like having cardiac stimulant and arrhythmia-inducing activity or side effects.

In the practice of the method of the invention, a quaternary ammonium salt compound is normally incorporated in a pharmaceutical carrier and the resulting composition is administered internally to an animal. In the present specification and claims, "pharmaceutical carrier" refers to known pharmaceutical excipients which are substantially non-toxic and non-sensitizing at dosage levels consistent with good antiarrhythmic activity. The active ingredient is preferably administered parenterally in the form of liquid injectable solutions or suspensions, and orally in the form of solid compositions which can be prepared by known techniques such as tableting and encapsulation. Suitable pharmaceutical carriers which can be employed for formulating the solid compositions include starch, lactose, glucose, sucrose, gelatin, powdered licorice, malt, rice flour, chalk, silica gel, hydroxyethyl cellulose, hydroxypropyl cellulose, magnesium carbonate, magnesium stearate, carboxymethyl cellulose, and the like and compatible mixtures thereof. The quaternary ammonium compounds can also be formulated as liquid compositions including syrups, elixirs, suspensions and emulsions for oral administration. Among the liquid pharmaceutical carriers which can be employed for orally-administered compositions are ethanol, water, saline, glucose syrup, syrup of acacia, mucilage of tragacanth, propylene glycol, polyethylene glycols, peanut oil, wheat germ oil, sunflower seed oil or corn oil and the like and compatible mixtures thereof. Orally-ingestible compositions can include emulsifying agents such as lecithin, sorbitan trioleate, polyoxyethylene sorbitan monooleate and natural gums such as gum acacia and gum tragacanth, and suspending agents such as polyethylene oxide condensation products of alkylphenols or fatty acids or fatty alcohols, or cellulose derivatives such as carboxymethyl cellulose or hydroxypropylmethyl cellulose. The compositions can also contain sweetening agents such as sucrose, or saccharin, flavoring agents such as caramel, coloring materials, preservatives and the like.

Injectable compositions adapted for parenteral administration such as intramuscular, subcutaneous or, preferably, intravenous injection can be prepared with pharmaceutical carriers which are liquid parenterally-acceptable vehicles, i.e., liquid pharmaceutical carriers which are adapted for use in formulating parenteral preparations and which are substantially non-toxic and nonirritating when administered parenterally at dosages consistent with good antiarrhythmic activity. Representative liquid parenterally-acceptable vehicles include pyrogen-free water, normal saline solutions, Ringer's Injection, Lactated Ringer's Injection, dextrose solutions, ethanol, propylene glycol, liquid polyethylene glycols, fixed vegetable oils such as corn oil, peanut oil or cottonseed oil, ethyl oleate, isopropyl myristate and the like. The injectable compositions can also contain other materials such as preservatives, buffers and the like. Preferred injectable compositions comprise a sterile solution of the quaternary ammonium salt compound in the parenterally-acceptable vehicle. The compositions can be formulated by using conventional procedures such as are described in Remington's Pharmaceutical Sciences, 13th Ed., Chapter 36, Mack Publ. Co., Easton, Pa. (1965).

The selection of the exact pharmaceutical carrier to be employed in any given circumstance can be carried out by routine and conventional range finding operations to arrive at formulations having the desired characteristics of physical form, ease of administration in a desired route, storage stability, etc.

The antiarrhythmic amount of the quaternary ammonium salt compounds to be administered to an animal can vary depending upon such factors as whether or not the animal is suffering from an arrhythmia at the time of administration, the type and severity of arrhythmia exhibited, the method and frequency of administration, the exact antiarrhythmic effect to be produced, the particular quaternary ammonium salt compound employed and the species, size, weight, age and physical condition of the particular animal being treated. In general, when the animal is actively exhibiting arrhythmia, it is preferred to administer the compound at an antiarrhythmic dosage rate sufficient to bring about a complete conversion of the arrhythmia to normal sinus cardiac activity. In such operations, the active compound is preferably introduced directly into the cardiovascular system of the animal to provide an antiarrhythmic concentration of the quaternary ammonium salt compound in the cardiovascular system, particularly at the heart. In a convenient procedure, the compound is administered by intravenous injection at an initial antiarrhythmic dosage less than that required to fully convert the arrhythmia to normal rhythm, and the heartbeat of the animal is monitored as the amount of compound administered is gradually increased over a period of minutes until an antiarrhythmic amount sufficient to fully convert the arrhythmia to rhythmic cardiac activity has been administered. It is then preferred to supply the compound in periodic maintenance antiarrhythmic dosages, such administration being either by the same parenteral route, or by administration of larger antiarrhythmic dosages by another route such as orally. The maintenance antiarrhythmic dosage and mode of administration are selected to provide a more-or-less continuous antiarrhythmic concentration of the quaternary ammonium salt compound in the cardiovascular system, such concentration being sufficient to inhibit further arrhythmia. In general, the quaternary ammonium compound can be administered intravenously in initial dosages of from about 0.1 or less to about 15 or more milligrams per kilogram of animal body weight, providing initial antiarrhythmic concentrations in the cardiovascular system. Maintenance dosages can vary widely depending upon a variety of factors such as the time and frequency of administration, the exact compound or compounds employed, the condition, size, age and species of the animal, the route of administration selected, the type of dosage form employed, the type and cause of the arrhythmia, and the length of time during which a maintenance dose is desired. In cases in which there is little or no likelihood of recurrence of arrhythmia once conversion has been brought about, the maintenance dosage can comprise a continuation of the initial intravenous antiarrhythmic dosage for a relatively brief period. When recurrence of arrhythmia is likely, the maintenance dosage can comprise repeated oral administration of an antiarrhythmic amount of the compounds over extended periods. Maintenance dosages can be administered by single or multiple doses provided that the compounds are administered in an antiarrhythmic amount sufficient substantially to alleviate cardiac arrhythmia.

A preferred group of the quaternary ammonium salt compounds comprises the compounds corresponding to the above formula I wherein $R_1$ and $R_2$ are both methyl or both ethyl, wherein Y is amino and wherein $X_1$ and $X_2$ are both bromine or both chlorine. It is also generally preferable that the moieties $R_1$ and $R_2$ together contain from 2 to 6 carbon atoms; that the moiety $R_3$ contain from 3 to 7 carbon atoms and that $R_1$, $R_2$ and $R_3$ together contain from 5 to 9 carbon atoms. Other preferred groups of compounds include those wherein Y is amino, $R_3$ is lower alkenyl or lower alkynyl of 3 or 4 carbon atoms or those wherein $R_3$ is substituted lower alkyl, lower alkenyl or lower alkynyl of from 2 to 4 carbon atoms substituted with a single bromo, chloro, keto or nitrilo substituent, and those wherein $R_3$ is benzyl, monohalobenzyl and dihalobenzyl. A further preferred group comprises the compounds corrsponding to the above formula wherein n is 2, Y is amino, $X_1$ and $X_2$ are bromine, $R_1$ and $R_2$ are methyl, and $R_3$ is lower alkenyl or lower alkynyl of 3 or 4 carbon atoms, and $A^-$ is chloride or bromide anion. This latter group of quaternary ammonium salts thus corresponds to the formula

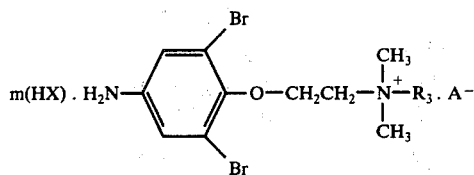

wherein m, HX and $A^-$ have the significance set out above with respect to formula I and $R_3$ is lower alkenyl or lower alkynyl of 3 or 4 carbon atoms, preferably 2-propynyl, allyl or 2-methylallyl. The preferred compounds of Formula Ia provide excellent antiarrhythmic results of long duration when administered orally or parenterally in relatively low dosages and are particularly preferred for combatting cardiac arrhythmias.

Preparation of the Compounds

The quaternary ammonium salt compounds of the invention can be prepared by the reaction of a tertiary amine compound corresponding to formula II

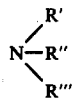

with a substituted organic alkylating agent corresponding to formula III

In the above formula Ii and III, one of the substituent moieties R', R", R''', and R'''' represents a substituted phenoxyalkyl moiety corresponding to formula IV

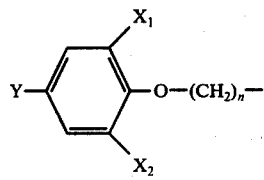

wherein $X_1$, $X_2$, Y and n all have the significance set out above with respect to formula I; and each of the remaining substituent moieties R', R", R''' and R'''' represents a different individual one of the moieties $R_1$, $R_2$ and $R_3$ as set out above with respect to formula I and B represents a pharmaceutically-acceptable strongly anionic moiety such as halide, alkyl or aryl sulfonate, sulfate or phosphate. Thus the substituted phenoxyalkyl moiety of formula IV can be provided as a substituted phenoxyalkylamine or as a substituted phenoxyalkyl halide, and the $R_1$, $R_2$ and $R_3$ moieties similarly can be provided by a tertiary amine compound of formula II or by a substituted organic compound of formula IV. Representative tertiary amines which can be employed as starting materials include N-methyl-N-ethyl-N(2-propynyl) amine; dimethyl phenethylamine; N,N-diethyl-N-4-chlorobutylamine; N-2-butenyl dimethylamine; N-allylpyrrolidine; picoline, lutidine; quinuclidine; 3,5-dibromo-β-dimethylamino-p-phenetidine; 3,5-diiodo-β-(N-3-nitrilopropyl-N-ethyl)amino-p-phenetidine; 3-chloro-5-bromo-4-[2-(N-2,4,5-trichlorobenzyl-N-methyl amino)propoxy]-N-butyl aniline; N,N-diethyl-N-(2-methylallyl) amine; N-butyl-N-[3-(2,5-diiodophenyl)propyl]-N-[3-(2,6-dichloro-4-aminophenoxy)-propyl]amine; 3,5-dichloro-4-[3-(N-3-nitrilopropyl-N-methylamino)propoxy]-N,N-dimethylaniline; 3,5-dibromo-4-[β-N-(3-butynyl)-N-methyl amino ethoxy]-N-ethylaniline; N-[β(2-bromo-4-amino-6-iodophenoxy)-ethyl]-N-(2-methylallyl)-N-ethylamine; N-allylpiperidine; 3,5-dichloro-β-(N-isopropyl-N-methyl-)amino-p-phenetidine; and 3,5-dibromo-β-(N-3-ketobutyl-N-methyl)amino-p-phenetidine. Representative substituted organic compounds can include propargyl bromide, propargyl chloride, 3,5-dibromo-4-(2-bromoethoxy)aniline; 3,5-dichloro-4-(3-bromopropoxy) N,N-dimethylaniline, β-cyanoethyl tosylate; 1-(2-bromo-6-chlorophenoxy)-(2-bromoethane); propenyl chloride, chlorohexane, methyl bromide, ethylene dibromide, benzyl bromide, 3,4,5-trichlorophenethyl bromide, chloroacetone, 1,4-dichloro-2-butene, butyl bromide, 1-chloro-2-methyl propane, 1-chloro-3-cyanopropane, 1,1,3-trichloropropane, 1-bromo-4-phenylbutane, and 3,4,5-trichlorophenacyl bromide.

The reaction proceeds when the reactants are contacted and mixed, preferably in the presence of an inert organic liquid such as acetonitrile or dimethyl formamide as a reaction medium. In preparing the quaternary ammonium compounds of the invention, the substituted halophenoxyalkyl amine compound of formula II and the organic compound of formula III are selected from such compounds in which the R', R", R''', and R'''' moieties are such as to provide the $R_1$, $R_2$ and $R_3$ moieties desired in the quaternary product. The reaction proceeds readily at temperatures of from about 10° C. to about 100° C., and is preferably carried out at a temperature from about 25° C. to about 70° C. The exact proportions of the reactants to be employed are not critical, however the formation of one molar proportion of the quaternary ammonium salt product requires one molar proportion of each of the tertiary amine and substituted organic reactants, and the reactants are preferably employed in such proportions. The reaction of the tertiary amine and organic compound proceeds with the evolution of heat and the production of a quaternary ammonium salt product wherein the anionic moiety is the anionic moiety B of the organic compound of formula III. In those cases in which the product separates as a precipitate in the reaction mixture, the product can be separated by conventional procedures such as filtration, decantation, centrifugation. In cases in which the product does not precipitate from the reaction mixture, the quaternary ammonium salt can be separated by other conventional procedures such as evaporation under reduced pressure, cooling of the reaction mixture and scratching or seeding to induce crystallization, dilution with organic liquids such as ethyl acetate, benzene or butyl acetate or the like. The product can be purified by conventional procedures such as recrystallization and washing.

The anionic moiety $A^{3l}$ of the quaternary ammonium salts corresponding to formula I can be varied by conversion of one salt to another by conventional procedures for anion exchange. The exchange can be carried out, for example, by the methathetic reaction of one of the quaternary ammonium salts of the invention with the desired anion in the presence of a cation which forms a methathesis reaction product with the anionic moiety to be replaced, said methathesis reaction product being insoluble in the reaction medium employed for the methathetic reaction. In a convenient procedure a quaternary ammonium halide of the invention is prepared as described above using a reactant corresponding to formula III wherein A is halogen, such as chlorine or bromine. The quaternary ammonium halide is dissolved in aqueous ethanol at room temperature and the solution is mixed with an aqueous solution of an acid supplying the desired anion, e.g., sulfuric acid. The halide is removed as hydrogen halide by fractional distillation and the metathesis quaternary ammonium salt product is separated and purified by conventional procedures. Alternatively, different anionic moieties can be introduced into the quaternary ammonium salt compounds of formula I by passing an aqueous solution of a compound of formula I through an anion-exchange resin saturated with the anion desired in the product.

In the preparation of the quaternary ammonium salts of the invention wherein $R_1$, $R_2$ and $R_3$ represent a quinuclidine, pyridine, picoline or lutidine residue, the substituted phenoxyalkyl moiety is conveniently supplied as a substituted phenoxyalkyl halide. The tertiary amine reactant is a substituted nitrogen-containing heterocyclic amine such as quinuclidine, pyridine, α-picoline, 3,4-dimethyl pyridine or the like. The quaternization reaction is conveniently carried out under substantially the conditions described above.

The pharmaceutically-acceptable acid addition salt form of the quaternary ammonium compounds, that is, those quaternary ammonium salts of formula I wherein m is one, are prepared according to conventional procedures for forming acid addition salts of primary, secondary or tertiary amines. In a convenient procedure, a quaternary ammonium salt corresponding to formula I wherein m is zero is taken up in a minimal amount of a lower alkanol and the mixture is treated with an excess of the desired pharmaceutically-acceptable acid in ether or dioxane. The salt is separated and purified by conventional procedures.

In a convenient procedure for the preparation of the quaternary ammonium salts of the invention wherein $R_1$ and $R_2$ represent lower alkyl, the tertiary amine reactant employed is a substituted 3,5-dihalophenoxy alkylamine corresponding to the above formula II wherein R' and R'' represent the $R_1$ and $R_2$ lower alkyl moieties as described above with respect to formula I and R''' represents a substituted phenoxyalkyl moiety corresponding to the above formula IV. Such tertiary amine starting materials can be prepared readily by the reaction of a substituted phenoxyalkyl halide with a dialkyl amine by the procedures described in U.S. Pat. No. 3,389,171 or by analogous procedures. The substituted organic compound reactant employed is a compound of formula III above wherein R'''' represents $R_3$ as described with respect to formula I and B represents halo, alkyl sulfonyl or aryl sulfonyl. In such procedure, the substituted halophenoxyalkylamine is dispersed in an inert organic liquid such as dimethylformamide or acetonitrile, and an equimolar proportion of the organic compound of formula III is added gradually and mixed therewith. The reaction mixture is maintained at a temperature within the reaction temperature range for a period of 1 to 36 hours. In those cases in which the product does not separate from the reaction mixture, the product can be conveniently separated by diluting the reaction mixture with several volumes of ethyl acetate. In those cases in which a crystalline product is not obtained upon dilution with ethyl acetate, the product can be crystallized by treating the ethyl acetate mixture with excess pharmaceutically-acceptable acid, trituration, or crystallization from other organic liquids such as methanol, ethanol, or isopropanol. The product can be purified by conventional procedures such as recrystallization and washing.

DESCRIPTION OF PREFERRED EMBODIMENTS

The following examples are illustrative of the invention.

EXAMPLE 1

3,5-Dibromo-β-dimethylamino-p-phenetidine (25.4 grams; 0.075 mole) is dissolved in 200 milliliters of acetonitrile at room temperature. 2-Methylallyl chloride (6.9 grams; 0.075 mole) is rapidly added dropwise to the solution with stirring, during which time a temperature rise of 3°–4° C. is observed. The reaction mixture is heated at a temperature of 55°–65° C. for 4 hours with continued stirring. Formation of a precipitate is observed in the mixture, beginning about 15 minutes after addition of the 2-methallyl chloride and continuing through the heating period. The reaction mixture is then cooled in an ice bath and filtered. The [2-(4-amino-2,6-dibromophenoxy)ethyl]dimethyl-(2-methylallyl-)ammonium chloride product is collected as a filter cake, dried in air and found to melt at 185°–186° C. The product is dissolved in hot isopropanol and the solution treated with activated carbon and filtered. The solution is cooled, whereupon a crystalline solid precipitate forms, and filtered. The purified [2-(4-amino-2,6-dibromophenoxy)ethyl]-dimethyl(2-methylallyl) ammonium chloride product is collected as a filter cake, dried under reduced pressure, and found to melt at 181°–182° C. The structure of the product, corresponding to the formula:

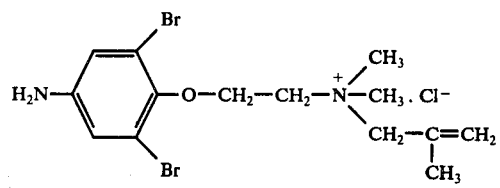

is confirmed by infrared and nuclear magnetic resonance spectroscopy. The product is found by combustion analysis to have carbon, hydrogen and nitrogen contents of 39.35, 4.98 and 6.64 percent, respectively, as compared with the theoretical contents of 39.2, 4.94 and 6.54 percent, respectively, calculated for the named structure.

EXAMPLE 2

3,5-Dibromo-β-dimethylamino-p-phenatidine (16.9 grams; 0.05 mole) is dissolved in 50 milliliters of dimethyl formamide at a temperature of about 25° C. To this solution is added dropwise with stirring ethyl bromoacetate (9.2 grams; 0.055 mole). During the addition the mixture warms spontaneously to a temperature of about 49° C., and the mixture is cooled to 27° C. prior to addition of the final 2 grams of ethyl bromoacetate. A precipitate forms in the reaction mixture after the addition is complete, and 50 milliliters of additional dimethyl formamide is added. The mixture is stirred for one hour, then held over night at room temperature. The crystalline solid product is collected as a filter cake by suction filtration of the mixture and the filter cake is recrystallized from boiling ethanol. The [2-(4-amino-2,6-dibromophenoxy)ethyl]dimethyl(ethyl carboxymethyl) ammonium bromide is obtained as a light tan crystalline solid, melting at 187°–188° C. The product is found by combustion analysis to have carbon, hydrogen and nitrogen contents of 33.5, 4.3 and 5.6 percent, respectively, as compared with the theoretical contents of 33.3, 4.2 and 5.6 percent, respectively, calculated for the named structure. The structure of the product is confirmed by infrared spectroscopy and nuclear magnetic resonance analysis.

A second crop of the product is obtained by diluting the dimethyl formamide reaction mixture filtrate with excess ethyl acetate, and collecting the resulting precipitate by filtration. This crop of the product is dried, crystallized from acetonitrile and found to have nuclear magnetic resonance and infrared spectra consistent with the assigned structure, and in excellent agreement with the spectra obtained with the first crop.

EXAMPLE 3

3,5-Dibromo-β-dimethylamino-p-phenetidine (20.3 grams; 0.06 mole) and 2-chlorobenzyl chloride (9.7 grams; 0.06 mole) are dissolved in 200 milliliters of acetonitrile. The reaction mixture is heated at a temperature of about 35° C. for about one hour and then at ambient temperature overnight with continued stirring. Formation of a precipitate is observed in the mixture, beginning about one hour after initial contacting of the reactants. The reaction mixture is filtered, and the [2-(4-amino-2,6-dibromophenoxy)ethyl]dimethyl(2-chlorobenzyl)ammonium chloride product is collected as a filter cake, dried in air, and recrystallized from isopropanol. The purified [2-(4-amino-2,6-dibromophenoxy)ethyl]dimethyl(2-chlorobenzyl)ammonium chloride product is found to melt at 172°–173° C. The structure of the product is confirmed by infrared and nuclear magnetic resonance spectroscopy. The product is found by combustion analysis to have carbon, hydrogen and nitrogen contents of 41.3, 4.3 and 5.8 percent, respectively, as compared with the theoretical contents of 40.9, 4.0 and 5.6 percent, respectively, calculated for the named structure.

EXAMPLE 4

3,5-Dibromo-β-dimethylamino-p-phenetidine (16.9 grams; 0.05 mole) is dissolved in 35 milliliters of dimethyl formamide and the solution is cooled in an ice-bath to a temperature of about 10° C. To this solution is added dropwise with stirring propargyl bromide (6.5 grams; 0.055 mole). During the addition the mixture warms spontaneously to a temperature of about 18° C., and the mixture is cooled to 10° C. prior to addition of the final amounts of propargyl bromide. The mixture is allowed to warm to room temperature then heated at a temperature of 45° C. for 1 hour and diluted with ethyl acetate, whereupon the crystalline solid product separates. The product is separated by filtration of the mixture, recrystallized once from a mixture of isopropanol and ethanol and recrystallized a second time from a mixture of ethanol and ethyl acetate. The [2-(4-amino-2,6-dibromophenoxy)ethyl]dimethyl(2-propynyl)ammonium bromide product is obtained as a yellow crystalline solid melting at 166°–168° C. The product is found by combustion analysis to have carbon, hydrogen and bromide contents of 34.5, 3.8 and 52 percent, respectively, as compared with the theoretical contents of 34.2, 3.8 and 52.5 percent, respectively, calculated for the named structure. The structure of the product is confirmed by infrared spectroscopy and nuclear magnetic resonance analysis.

EXAMPLE 5

3,5-Dibromo-β-dimethylamino-p-phenetidine (25.4 grams; 0.075 mole) is dissolved in 200 milliliters of acetonitrile at room temperature. Chloroacetone (7.0 grams; 0.075 mole) is rapidly added dropwise to the solution with stirring, during which time a slight temperature rise is observed. The reaction mixture is heated at a temperature of 55°–65° C. for 4 hours with continued stirring, then cooled in an ice bath and filtered. The [2-(4-amino-2,6-dibromophenoxy)ethyl]dimethyl-(acetonyl)ammonium chloride product is collected as a filter cake, dried in air, and recrystallized from isopropanol. The purified [2-(4-amino-2,6-dibromophenoxy)ethyl]dimethyl(acetonyl)ammonium chloride product is obtained as a tan crystalline solid melting at 181°–182° C. The structure of the product is confirmed by infrared and nuclear magnetic resonance spectroscopy. The product is found by combustion analysis to have carbon, hydrogen and nitrogen contents of 36.1, 4.6 and 6.4 percent, respectively, as compared with the theoretical contents of 36.3, 4.5 and 6.5 percent, respectively, calculated for the named structure.

EXAMPLE 6

3,5-Dibromo-β-dimethylamino-p-phenetidine (16.9 grams; 0.05 mole) is dissolved in 35 milliliters of dimethyl formamide at a temperature of about 25° C. Allyl bromide (6.7 grams; 0.055 mole) is added dropwise to the solution with stirring. During the addition the mixture warms spontaneously to a temperature of about 32° C. The mixture is then held overnight at room temperature. The mixture is diluted with a large excess of ethyl acetate, whereupon a yellow amorphous solid separates. The solid product is separated by decantation, washed with ethyl acetate and crystallized by trituration with isopropanol. The product is recrystallized once from hot isopropanol and a second time from an ethanol-ethyl acetate mixture. The [2-(4-amino-2,6-dibromophenoxy)ethyl]dimethyl(allyl)ammonium bromide product is obtained as a yellow crystalline solid melting at 157.5°–159° C. The product is found by combustion analysis to have carbon, hydrogen and bromine contents of 33.8, 4.2 and 52.0 percent, respectively, as compared with the theoretical contents of 34.0, 4.2 and 52.2 percent, respectively, calculated for the named structure. The structure of the product is confirmed by infrared spectroscopy and nuclear magnetic resonance analysis.

EXAMPLES 7-14

In procedures similar to those employed in Examples 1-6 above, 2,6-dibromo-β-dimethylamino-p-phenetidine is quaternized with appropriate organic alkylating reactants to produce quaternary ammonium salt compounds of the invention. The compounds correspond to formula I above wherein m is zero, Y is amino, n is 2, $X_1$ and $X_2$ are both bromo and $R_1$ and $R_2$ are methyl. The compounds obtained, identified by the $R_3$ and $A^-$ moieties, and the organic reactants reacted with the said phenetidine compounds are set out in the following table.

| Ex. | $R_3$ | $A^-$ | Melting Point ° C. | Alkylating Reactant |
|---|---|---|---|---|
| 7 | 2-hydroxyethyl | bromide | 228°–229° | ethylenebromohydrin |
| 8 | 3,4-dichlorophenacyl | bromide | 212°–214° | 3,4-dichlorophenacylbromide |
| 9 | phenethyl | bromide | 209°–210° | β-bromoethylbenzene |
| 10 | 3-chloropropen-2-yl | chloride | 168°–169° | 1,3-dichloropropene |
| 11 | benzyl | bromide | 198°–199° | benzyl bromide |
| 12 | 4-chlorobenzyl | chloride | 187°–188° | 4-chlorobenzyl chloride |
| 13 | 2,4-dichlorobenzyl | chloride | 172°–173° | 2,4-dichlorobenzyl chloride |
| 14 | 3,4-dichlorobenzyl | chloride | 158.5°–160° | 3,4-dichlorobenzyl chloride |

EXAMPLE 15

3,5-Dichloro-β-dimethylamino-p-phenetidine (15 grams) and 2-methylallyl chloride (5.6 grams) are dissolved in 140 milliliters of acetonitrile. The reaction mixture is heated at a temperature of about 60°–65° C. for 32 hours and then cooled. The reaction mixture is filtered, and the [2-(4-amino-2,6-dichlorophenoxy)ethyl]dimethyl(2-methylallyl)-ammonium chloride product is collected as a filter cake, washed with acetonitrile and dried. The purified [2-(4-amino-2,6-dichlorophenoxy)ethyl]dimethyl(2-methylallyl)-ammonium chloride product is found to melt at 189°–191° C.

EXAMPLE 16

3,5-Dibromo-β-diethylamino-p-phenetidine (14 grams; 0.038 mole) and 4.85 grams of allyl bromide are dissolved in 140 milliliters of acetonitrile. The mixture is heated with stirring at a temperature of 60°–65° C. for 4 hours, stirred at room temperature overnight, then heated at 60°–65° C. for about 18 hours and cooled. The crystalline product is separated by filtration of the mixture and the [2-(4-amino-2,6-dibromophenoxy)ethyl]diethyl(allyl)ammonium bromide product is obtained as a crystalline solid melting at 205°–207° C.

EXAMPLE 17

3,5-Dibromo-4(3-dimethylaminopropoxy)aniline (5 grams) and 1.8 grams of allyl bromide are mixed with 30 milliliters of acetonitrile. Crystal formation and a slight temperature rise is observed. The reaction mixture is heated at a temperature of 50°–60° C. for 4 hours with stirring, then held overnight and filtered. The [3-(4-amino-2,6-dibromophenoxy)propyl]dimethyl(allyl)ammonium bromide product is collected as a filter cake, dried in air, and obtained as a buff colored crystalline solid melting at 167°–169° C.

EXAMPLE 18

3,5-Dibromo-β-dimethylamino-phenetidine (13.5 grams; 0.04 mole) is dissolved in 150 milliliters of ethyl acetate at room temperature. Cyanomethyl benzenesulfonate (8 grams; 0.04 mole) is added dropwise to the solution with stirring. The reaction mixture is held overnight at room temperature. The reaction mixture is filtered. The [2-(4-amino-2,6-dibromophenoxy)ethyl]dimethyl(2-nitriloethyl)-ammonium benzenesulfonate product is collected as a filter cake. The product is taken up in hot acetonitrile and the solution is filtered. The hot filtrate is cooled, whereupon a crystalline solid precipitate forms, and filtered. The purified [2-(4-amino-2,6-dibromophenoxy)ethyl]dimethyl(2-nitriloethyl]ammonium benzenesulfonate product is collected as a filter cake, air dried, and found to melt at 173.5°–175° C. The structure of the product is confirmed by infrared and nuclear magnetic resonance spectroscopy. The product is found by combustion analysis to have carbon, hydrogen and nitrogen contents of 40.6, 3.93 and 7.87 percent, respectively, as compared with the theoretical contents of 40.39, 3.96 and 7.85 percent, respectively, calculated for the named structure.

EXAMPLE 19

3,5-Dibromo-β-dimethylamino-p-phenetidine (25.4 grams; 0.075 mole) is dissolved in 300 milliliters of acetonitrile at room temperature. Allyl methanesulfonate (10.2 grams; 0.075 mole) is rapidly added to the solution with stirring. The reaction mixture is heated at a temperature of 35°–45° C. for 5 hours with continued stirring. Formation of a precipitate is observed in the mixture, beginning about 10 minutes after addition of the allyl methanesulfonate and continuing through the heating period. The reaction mixture is cooled and filtered. The [2-(4-amino-2,6-dibromophenoxy)-ethyl]dimethyl(allyl)ammonium methanesulfonate product is collected as a filter cake, dried, and recrystallized from n-propanol. The product is found to melt at 202°–203° C. The structure of the product is confirmed by infrared and nuclear magnetic resonance spectroscopy. The product is found by combustion analysis to have carbon, hydrogen and nitrogen contents of 35.35, 4.65 and 6.13 percent, respectively, as compared with the theoretical contents of 35.45, 4.68 and 5.91 percent, respectively, calculated for the named structure.

EXAMPLE 20

α3,5-Tribromo-p-phenetidine (20.2 grams) is dissolved in 150 milliliters of acetonitrile, then mixed with a solution of 6 grams of quinuclidine in 100 milliliters of acetonitrile. The reaction mixture is heated at a temperature of about 50° C. for 4 hours and then cooled, and held for 48 hours at ambient temperature. The reaction mixture is filtered, and the [2-(4-amino-2,6-dibromophenoxy)-ethyl]quinuclidinium bromide product is collected as a filter cake, washed with acetonitrile and dried. The purified [(2-(4-amino-2,6-dibromophenoxy)ethyl]quinuclidinium bromide product is found to melt at 239°-241° C. The product corresponds to the formula:

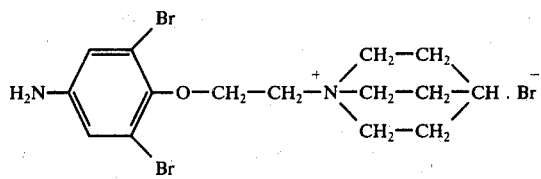

EXAMPLE 21

3,5-Dibromo-β-pyrrolidino-p-phenetidine (15 grams) and allyl bromide (5.25 grams) are mixed in 50 milliliters of acetonitrile. The reaction mixture is heated at a temperature of about 60°-70° C. for 4 hours and then cooled. The reaction mixture is diluted with ethylacetate, and the [2-(4-amino-2,6-dibromophenoxy)ethyl]allyl pyrrolidinium bromide product is collected by decantation. The product is taken up in isopropanol, mixed with excess hydrogen bromide in isopropanol and the mixture is cooled and filtered. The 1-[2-(4-amino-2,6-dibromophenoxy)ethyl]-1-allyl-pyrrolidinium bromide hydrobromide product is found to melt at 211°-213° C.

EXAMPLE 22

In a procedure similar to that described in Example 21, 1-[2-(4-amino-2,6-dibromophenoxy)ethyl]-1-allyl piperidinium bromide hydrobromide, melting at 207°-209° C., is prepared by reacting 17 grams of 3,5-dibromo-β-piperidino-p-phenetidine and 5.75 grams of allyl bromide in 50 milliliters of acetonitrile.

EXAMPLE 23

3,5-Dibromo-β-hexamethyleneamino-p-phenetidine (16.8) grams) and allyl bromide (5.47 grams) are dissolved in 70 milliliters of acetonitrile. The reaction mixture is heated at a temperature of about 60° C. for 2 hours and then cooled. The reaction mixture is filtered, and the [2-(4-amino-2,6-dibromophenoxy)ethyl]-1-allyl-hexahydroazepinium bromide product, corresponding to the formula

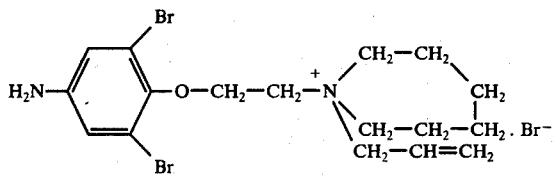

is collected as a filter cake, washed with acetonitrile and dried. The purified product is found to melt at 177°-179° C.

EXAMPLE 24

In a procedure similar to that described above in Example 20, β, 3,5-tribromo-p-phenetidine and 3-picoline are reacted together to prepare 1-[2-(4-amino-2,6-dibromophenoxy)ethyl]-3-picolinium bromide, melting at 218°-220° C.

EXAMPLE 25

In a procedure similar to that of Example 17, 3,5-dibromo-4'-(4-dimethylaminobutoxy) aniline is reacted with allyl bromide to prepare [4-(4-amino-2,6-dibromophenoxy)-butyl]dimethyl(allyl) ammonium bromide as a pale yellow crystalline solid melting at 184°-186° C.

In procedures similar to those described above in Examples 1-25, the following quaternary ammonium salt compounds are prepared:

1-[3-(4-ethylamino-2,6-dibromophenoxy)propyl]-1-allyl-2-methyl pyrrolidinium bromide hydrobromide;

[4-(4-dimethylamino-2,6-dichlorophenoxy)butyl]-dibutyl(3-butynyl)ammonium methanesulfonate;

1-[2-(4-amino-2,6-diiodophenoxy)ethyl]-3,4-dimethyl pyridinium bromide hydrobromide;

[3-(4-hexylamino-2,6-dichlorophenoxy)propyl]-dimethyl-(4-nitrilobutyl)ammonium chloride;

[2-(4-amino-2,6-dibromophenoxy)ethyl]diethyl(3-butenyl)ammonium p-toluenesulfonate;

[2-(4-amino-2,6-diiodophenoxy)ethyl]dimethyl[4-(3,4-dichlorophenyl)butyl]ammonium chloride;

1-[3-(4-ethylamino-2,6-dichlorophenoxy)propyl]-1-(2-propynyl)-hexahydroazepinium chloride hydrochloride; and

[2-(4-amino-2,6-dibromophenoxy)ethyl]dimethyl(3-keto butyl)ammonium benzenesulfonate.

The following examples further illustrate the invention, particularly as to the use of the compounds in controlling cardiac arrhythmias.

EXAMPLE 26

Ventricular tachycardia is produced in dogs in a method similar to the method of Lucchesi and Hardman (J. Pharmacol. Exptl. Therap., 132, 372, 1961) by the administration of ouabain. In such operations, a dog is anesthetized by the intravenous administration of pentobarbital sodium at a dosage rate of 30 milligrams per kilogram. A femoral artery is cannulated with polyethylene tubing for measurements of blood pressure. A femoral vein is similarly cannulated for administration of ouabain and administration of the test compound. Hypodermic needle electrodes are employed for recording electrocardiograms. In such operations, ouabain is administered intravenously by infusion at a constant rate via the cannulated femoral vein. The infusion rate is 35 micrograms of ouabain per kilogram of animal body weight per hour. Within 1 to 1.5 hours following the start of the infusion, a ventricular tachycardia is seen to develop.

After ventricular tachycardia is observed, a test compound is administered intravenously by administration of varying amounts of a composition comprising 50 milligrams of the test compound as a sterile solution in 10 milliliters of water containing 0.9 percent sodium chloride. Each dose is administered slowly over a period of 15 to 30 seconds. The compound is administered at an initial dosage rate of 0.25 milligram of test compound per kilogram of animal body weight. Blood pressure and electrocardiogram are observed for five minutes after administration. When a complete conversion from the arrhythmic condition to normal sinus rhythm is not observed within the 5 minute period, a second dose of 0.50 milligram of the test compound per kilogram is administered by a similar procedure and blood pressure and heartbeat are similarly observed for 5 minutes. When complete conversion of the ventricular tachycardia to normal sinus rhythm is not observed, the dosage is increased two-fold every five minutes until complete conversion is obtained. The animal is then observed and the duration of the period of normal cardiac rhythm produced by administration of the test compound is recorded as the duration of antiarrhythmic activity. The termination of the period of normal activity is marked by the reappearance of ventricular tachycardia or fibrillation as indicated by the electrocardiogram observations. The antiarrhythmic dosage of test compound sufficient to bring about a complete conversion of the ouabain-induced tachycardia, and the duration of the period of normal cardiac activity are set out below.

| Cmpd. of Ex. No. | Conversion Dose (Milligrams per Kilogram) | Duration in Minutes |
| --- | --- | --- |
| 1 | 0.5 | 15 |
| 2 | 1 | 2.6 |
|   | 2 | 3.5 |
| 3 | 1 | 12.5 |
| 4 | 0.5 | 24 |
| 5 | 1 | 11 |
| 6 | 1 | 6 |
| 7 | 1 | 25 |
| 8 | 16 | 10 |
| 9 | 2 | 3.5 |
| 10 | 1 | 3 |
| 11 | 1 | 8.5 |
| 12 | 1 | 9.5 |
| 13 | 0.5 | 4 |
| 14 | 2 | 14 |
| 15 | 0.5 | 4.5 |
| 16 | 2 | 6.5 |
| 17 | 1 | 6 |
| 18 | 1 | 4 |
| 19 | 1 | 17.5 |
|   | 2 | 39.0 |
| 20 | 0.5 | 1 |
| 21 | 2 | 1.5 |
| 22 | 1 | 6.5 |
| 23 | 0.5 | 3.3 |
|   | 1 | 7.5 |
| 24 | 0.5 | 38 |
| 25 | 2 | 26 |

EXAMPLE 27

The procedure of Example 26 is repeated, employing the compound of Example 1, [2-(4-amino-2,6-dibromophenoxy)-ethyl]-dimethyl(2-methylallyl)ammonium chloride, as a test compound. In these operations two groups of three dogs each are administered the test compound intravenously at antiarrhythmic dosage rates of 1 and 2 milligrams per kilogram after ectopic ventricular rhythms have been established by continuous infusion of ouabain. Complete conversion of the arrhythmias to sinus rhythm is observed in all the dogs, with means durations of sinus rhythm of 12.7 and 26.5 minutes, respectively, being observed in the groups administered 1 and 2 milligrams of the test compound, respectively, per kilogram.

EXAMPLE 28

[2-(4-(Amino-2,6-dibromophenoxy)ethyl]dimethyl-(2-methylallyl)ammonium chloride is employed to alleviate multifocal ventricular arrhythmias induced by administration of n-hexane and epinephrine. In these operations, dogs are anesthetized by intravenous administration of 30 milligrams of pentobarbital sodium per kilogram. Transient ventricular arrhythmias are induced by a modification of the method of Garb and Chenowith, J. Pharmacol. Exp. Ther. 94; 12 (1948) in which the heart is sensitized by intratracheal injection of 0.04 milliliter of n-hexane per kilogram, followed in 15 seconds by rapid intravenous administration of 1-epinephrine bitrate at a dosage rate of 10 micrograms per kilogram. Such procedure produces a transient arrhythmia lasting about 10 seconds. Duration of protection by a test compound is evaluated by repeating the n-hexane and epinephrine challenge periodically and monitoring electrocardiogram and arterial blood pressure. In such operations the above-named quaternary ammonium compound is found to give excellent protection against the arrhythmias when administered intravenously at a dosage rate of one milligram per kilogram, the duration of antiarrhythmic effect lasting about 1 hour. When the same compound is administered at a dosage rate of 2 milligrams per kilogram, the duration of protection is found to be greater than 2 hours.

In similar operations, dosages of 5 to 10 milligrams per kilogram are found to be required to obtain similar antiarrhythmic effects when the known antiarrhythmic agent, quinidine sulfate, is employed as a test compound.

In other operations carried out by procedures similar to that described by Bacaner, American Journal of Cardiology, 21, 504 (1968); the intravenous administration of [2-(4-amino-2,6-dibromophenoxy)ethyl]dimethyl(2-methylallyl) ammonium chloride to electrically paced dogs is found to provide substantial increases in the threshold for electrically induced ventricular fibrillation.

EXAMPLE 29

An experimental occlusion of the anterior descending coronary artery is produced in dogs according to the method of Harris, Circulation 1, 1318 (1950). Following surgery the animals are given a penicillin-streptomycin preparation and allowed to recover for 18-24 hours. The animals are given 3 milligrams per kilogram of morphine sulfate as an analgetic and sedative to allow handling. Electrocardiograms are recorded both before and after administration of [2-(2-amino-2,6-dibromophenoxy)ethyldimethyl(2-methylallyl)ammonium chloride to the test animals. The incidence of abnormal complexes (premature ventricular contractions and atrioventricular nodal beats) per minute is recorded as a percentage of total beats per minute. In one such operation the test compound is administered by intravenous infusion at rates of 1, 2, 2 and 2 milligrams per kilogram at intervals of 10 to 15 minutes. A marked decrease in heart beat rate is observed with a concomitant decrease in percentage of abnormal beats per minute following the first infusion. Following the last infusion of test compound the heartbeat rate is observed to have decreased from a rate of over 160 beats per minute prior to the first infusion to about 90–100 beats per minute. The incidence of ectopic beats at this time has decreased from a pretreatment level of 100 percent abnormal beats per minute to below 60 percent, reaching zero (100 percent normal beats) within about 10 minutes after the last infusion. The lower heartbeat rate and low incidence of abnormal beats (generally 0 to 20 percent of the total beats per minute are abnormal) is found to persist for 2 hours following the last infusion of test compound, at which time the experiment is terminated.

In similar operations, the same test compound is infused at dosages of 1, 2 and 4 milligrams per kilogram at intervals over a forty minute period. Prior to infusion the incidence of abnormal beats is 100 percent. Within about eight minutes following the last infusion, a substantially complete conversion to sinus rhythm is obtained. The incidence of abnormal beats is found to remain at zero with occasional brief periods of slight arrhythmia (2–5 percent abnormal beats) for 2.5 hours following the last dosage of the test compound, when recording is terminated. Resumption of recording 215 minutes later indicates that significant antiarrhythmic effects are still exhibited.

In a similar operation the [2-(2-amino-2,6-dibromophenoxy)ethyl]dimethyl(2-methylallyl)ammonium chloride is administered orally in gelatin capsules. The test compound is administered in multiple dosages of 30, 30 and 50 milligrams per kilogram over a period of 150 minutes. Periods of reduced frequency of abnormal heart beats are noted beginning 10 minutes after administration of the first dosage of test compound, the second and third doses providing further and more consistent antiarrhythmic effects. Beginning about 25 minutes after the last dose of the test compound is administered the electrocardiogram shows periods in which less than 10 percent of the beats are abnormal interspersed with occasional periods of arrhythmia. Antiarrhythmic effects continue to be observed until the recording is terminated 140 minutes after the last dose of test compound.

EXAMPLE 30

[2-(4-amino-2,6-dibromophenoxy)ethyl]dimethyl-(allyl)ammonium bromide is administered to mice intravenously and orally. The animals are thereafter sacrificed and blood and heart tissue analyses are carried out to ascertain the concentration of test compound present. In such operations mice intravenously administered the test compound at a rate of 6 milligrams per kilogram are found to have blood levels of 27 micrograms of test compound per milliliter 10 seconds after injection, 2.1 micrograms per milliliter 3 minutes after injection. Analysis of heart tissue indicates a concentration of 5.5 micrograms of test compound per gram of tissue 10 minutes after injection. Similar analyses are carried out with animals administered 6 milligrams of test compound per kilogram orally. Thirty minutes after oral administration, blood and heart levels of 1.1 and 5.1 micrograms, respectively, of test compound per milliliter of blood or gram of heart tissue, respectively, are found.

Similar operations carried out by administration of [2-(4-amino-2,6-dibromophenoxy)ethyl]dimethyl(2-methylallyl)-ammonium chloride to rabbits similarly indicate oral absorption of the test compound. Significant blood and heart levels of test compound are detected with both oral and intravenous administration.

EXAMPLE 31

An aqueous solution of [2-(4-amino-2,6-dibromophenoxy)ethyl]dimethyl (2-methylallyl)ammonium chloride is administered orally to several groups of male and female Sprague-Dawley derived rats and male and female Swiss mice (Cox strain). The compound is administered as single oral dosages in varying amounts, and the animals are held to assess toxicity 24 hours after administration of the compound. In such operations, the quaternary ammonium compound is found to have an $LD_{50}$ of 758 milligrams per kilogram (mg/kg) in the male rats; 725 mg/kg in the female rats, 560 mg/kg in the male mice, and 550 mg/kg in the female mice.

EXAMPLE 32

35 Grams of [2-(4-amino-2,6-dibromophenoxy)ethyl]-dimethyl (2-methylallyl)ammonium bromide is dissolved in 2 liters of sterile normal physiological saline solution. The solution is filtered and filled into 10 cubic centimeter (cc) syringes calibrated to permit injection of the parenteral preparation in 0.5 cc increments. The syringes are individually packaged in containers adapted to maintain sterility and sterilized. The parenteral dosage units are each adapted for parenteral administration of the active compound in increments of about 8.75 milligrams each to a total of 175 milligrams.

Similar parenteral preparations are prepared using 25 grams of [2-(4-amino-2,6-dibromophenoxy)ethyl](ethyl)methyl-(allyl) ammonium methane sulfonate in 1.5 liters of Lactated Ringer's Injection; 40 grams of 1-[2-(4-amino-2,6-diiodophenoxy)ethyl)](2-methylallyl)3,4-dimethylpyrrolidinium bromide hydrobromide in sterile distilled water containing 0.4 percent chlorobutanol preservative; and 10 grams of [3-(4-diethylamino-2,6-dichlorophenoxy)propyl]dimethyl(2-propynyl) ammonium chloride in one liter of Dextrose Injection.

EXAMPLE 33

100 Parts of [3-(4-amino-2,6-dichlorophenoxy)-propyl]dibutyl(3-butynyl)ammonium methanesulfonate and 35 parts of lactose are mixed well with 751 parts of starch. The mixture is filled into gelatin capsules in the amount of 0.4 grams per capsules are suitable for oral administration.

EXAMPLE 34

Tablets are prepared from a granulation comprising 50 parts by weight of [2-(4-amino-2,6-dibromophenoxy)ethyl] dimethyl(2-methylallyl)ammonium chloride, 100 parts lactose, 3.5 parts magnesium stearate, 170 parts starch, 50 parts microcrystalline cellulose, one part of a polyoxyethylene sorbitan monooleate surface active dispersing agent and 0.4 part of F.D.&C. approved color. The granulation is screened and compressed into tablets weighing about 0.287 gram each to prepare a composition in dosage unit form adapted for oral administration to animals. The dosage units are adapted to be employed in maintenance antiarrhythmic therapy to inhibit recurrence of arrhythmias in animals subject thereto, and prophylactically to animals in preparation for exposure to physical or chemical conditions creating a risk of cardiac arrhythmia. The tablets are administered to animals at the rate of one or two tablets (containing 50 milligrams of active antiarrhythmic agent) per day.

What is claimed is:

1. A composition useful as an antiarrhythmic comprising a pharmaceutical carrier and from about 0.01 to about 98 percent by weight of a quaternary ammonium compound corresponding to the formula

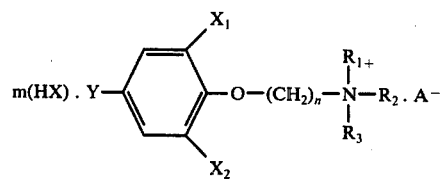

wherein Y represents amino, loweralkylamino or diloweralkylamino; $R_1$ and $R_2$ represent lower alkyl; $R_3$ represents acetonyl; $X_1$ and $X_2$ represent halogen; $A^-$ represents a stoichiometric equivalent quantity of a pharmaceutically-acceptable anion; $n$ represents one of the integers 2, 3 or 4; HX represents a stoichiometric equivalent quantity of a pharmaceutically-acceptable acid; and $m$ represents one of the integers zero and one.

2. The composition of claim 1 wherein the composition is a liquid parenterally-acceptable vehicle, and wherein the composition is a sterile solution of the quaternary ammonium compound in the vehicle.

3. The composition of claim 1 wherein the composition is in a dosage unit form adapted for oral administration to animals, each of said units containing from about 1 to about 500 milligrams of the quaternary ammonium salt compound.

4. A method for combatting cardiac arrhythmias which comprises administering to an animal a cardiac antiarrhythmic amount of a quaternary ammonium compound corresponding to the formula

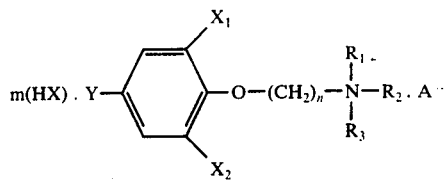

wherein Y represents amino, loweralkylamino or diloweralkylamino; $R_1$ and $R_2$ represent lower alkyl; $R_3$ represents acetonyl; $X_1$ and $X_2$ represent halogen; $A^-$ represents a stoichiometric equivalent quantity of a pharmaceutically-acceptable anion; $n$ represents one of the integers 2, 3 or 4; HX represents a stoichiometric equivalent quantity of a pharmaceutically-acceptable acid; and $m$ represents one of the integers zero and one.

5. The method of claim 4 wherein the quaternary ammonium compound is administered by intravenous injection to a mammal suffering cardiac arrhythmia.

6. The method of claim 4 wherein the quaternary ammonium compound is administered orally to a cardiac arrhythmic mammal.

* * * * *

UNITED STATES PATENT AND TRADEMARK OFFICE
CERTIFICATE OF CORRECTION

PATENT NO. : 4,057,645
DATED : November 8, 1977
INVENTOR(S) : Stanley J. Strycker It is certified that error appears in the above-identified patent and that said Letters Patent are hereby corrected as shown below:

Column 1, line 53, "intergers" should read --integers--.

Column 2, line 14, "aa" should read --as--.

Column 2, line 47, "cardiac arrhythmia" should read --"cardiac arrhythmia"--.

Column 3, line 1, "strohanthidin," should read --strophanthidin,--.

Column 5, line 17, "corrsponding" should read --corresponding--.

Column 5, line 55, "Ii" should read --II--.

Column 7, line 11, "$A^{31}$" should read --$A^-$--.

Column 12, line 65, "α3,5-Tribromo-p-phenetidine" should read --α,3,5-Tribromo-p-phenetidine--.

Column 13, line 6, "[(2-(4-amino-2,6-dibromophenox-" should read --[2-(4-amino-2,6-dibromophenox- --.

Column 15, line 52, "means" should read --mean--.

Column 15, line 58, "[2-(4-(Amino-2,6-dibromophenoxy)-ethyl]dimethyl-" should read --[2-(4-Amino-2,6-dibromophenoxy)-ethyl]dimethyl- --.

UNITED STATES PATENT AND TRADEMARK OFFICE
CERTIFICATE OF CORRECTION

PATENT NO. : 4,057,645
DATED : November 8, 1977
INVENTOR(S) : Stanley J. Strycker It is certified that error appears in the above-identified patent and that said Letters Patent are hereby corrected as shown below:

Column 16, line 41, "phenoxy)ethyldimethyl(2-methyl-allyl)ammonium" should read --phenoxy)ethyl]dimethyl(2-methyl-allyl)ammonium--.

Signed and Sealed this

Eighteenth Day of April 1978

[SEAL]

Attest:

RUTH C. MASON
Attesting Officer

LUTRELLE F. PARKER
Acting Commissioner of Patents and Trademarks